US012701286B2

(12) United States Patent
Teplitzky

(10) Patent No.: US 12,701,286 B2
(45) Date of Patent: Aug. 4, 2026

(54) ELECTROCARDIOGRAM WAVE SEGMENTATION USING MACHINE LEARNING

(71) Applicant: Preventice Solutions, Inc., Rochester, MN (US)

(72) Inventor: Benjamin A. Teplitzky, Rochester, MN (US)

(73) Assignee: BOSTON SCIENTIFIC CARDIAC DIAGNOSTICS, INC., Rochester, MN (US)

( * ) Notice: Subject to any disclaimer, the term of this patent is extended or adjusted under 35 U.S.C. 154(b) by 870 days.

(21) Appl. No.: 17/974,025

(22) Filed: Oct. 26, 2022

(65) Prior Publication Data

US 2023/0134114 A1 May 4, 2023

Related U.S. Application Data

(60) Provisional application No. 63/272,982, filed on Oct. 28, 2021.

(51) Int. Cl.
*A61B 5/349* (2021.01)
*A61B 5/366* (2021.01)
*H04N 21/426* (2011.01)
*H04N 21/61* (2011.01)

(52) U.S. Cl.
CPC .......... *H04N 21/426* (2013.01); *A61B 5/349* (2021.01); *A61B 5/366* (2021.01); *H04N 21/42676* (2013.01); *H04N 21/6118* (2013.01)

(58) Field of Classification Search
None
See application file for complete search history.

(56) References Cited

U.S. PATENT DOCUMENTS

| | | | | |
|---|---|---|---|---|
| 11,337,637 | B2 * | 5/2022 | Noseworthy | A61B 5/316 |
| 12,171,564 | B1 * | 12/2024 | Guo | A61B 5/7267 |
| 12,193,826 | B2 * | 1/2025 | Jiang | G06F 16/2379 |
| 12,310,760 | B2 * | 5/2025 | Toth | A61B 5/0205 |
| 12,369,837 | B2 * | 7/2025 | Dziubinski | A61B 5/327 |
| 2023/0137626 | A1 * | 5/2023 | Teplitzky | A61B 5/349 |
| | | | | 705/2 |

(Continued)

OTHER PUBLICATIONS

Filos et al. âBeat-to-beat P-wave morphology as a predictor of paroxysmal atrial fibrillationâ Computer Methods and Programs in Biomedicine vol. 151, Nov. 2017, pp. 111-121 (Year: 2017).*

(Continued)

*Primary Examiner* — Shirley X Jian
(74) *Attorney, Agent, or Firm* — Faegre Drinker Biddle & Reath LLP

(57) ABSTRACT

A method includes analyzing a first segment of electrocardiogram measurements corresponding to a first heartbeat and a second heartbeat of a patient to identify a set of features of the first segment of electrocardiogram measurements. The method further includes adjusting the set of features based at least on the first segment and a second segment of electrocardiogram measurements corresponding to the first heartbeat. The method further includes predicting, based on the adjusted set of features, a region in the second segment of electrocardiogram measurements comprising a p-wave generated by the second heartbeat.

20 Claims, 8 Drawing Sheets

<u>800</u>

(56) References Cited

U.S. PATENT DOCUMENTS

| | | | | |
|---|---|---|---|---|
| 2023/0172564 A1* | 6/2023 | Zlochiver | .............. | A61B 5/353 |
| | | | | 600/515 |
| 2025/0143623 A1* | 5/2025 | Lin | ......................... | A61B 5/366 |
| 2025/0204866 A1* | 6/2025 | Ramani | ................... | A61B 5/349 |

OTHER PUBLICATIONS

MarÅ¡Ã¡, novÃ¡, L., NÄmcovÃ¡, A., SmÃ-Å¡ek, R. et al. Advanced P Wave Detection in Ecg Signals During Pathology: Evaluation in Different Arrhythmia Contexts. Sci Rep 9, 19053 (2019) (Year: 2019).*

International Search Report and Written Opinion for International patent application No. PCT/US2022/047852, filed Oct. 26, 2022, mailed Feb. 8, 2023.

Rao MV Achutch et al. "P- and T-wave delineation in ECG signals using parametric mixture Gaussian and dynamic programming," Biomedical Signal Processing and Control, vol. 51 May 12, 2019; pp. 328-337, XP085651241, ISSN: 1746-8094, DOI: 10.1016/J. BSPC.2019.03.001 passage bridging col. 1 and 2 of p. 330; figure 1, p. 330, col. 2, section "Smoothing and peak/valley picking" p. 330, section 2.2. "The second prior assumes . . . " passage bridging p. 330 and 331; section 2.2.7.

Pemankar Abdolrahman et al. "An Ensemble of Deep Recurrent Neutral Networks for P wave Detection in Electrocardiogram," ICASSP 2019-2019 IEEE International Conference on Acoustics, Speech and Signal Processing (ICASSP), IEEE, May 12, 2019, pp. 1284-1288, XP033564890, DOI: 10.1109/ICASSP: 2019.8682307 [retrieved on Apr. 4, 2019] abstract.

* cited by examiner

ELECTROCARDIOGRAM WAVE SEGMENTATION USING MACHINE LEARNING

CROSS-REFERENCE TO RELATED APPLICATION

This application claims priority to Provisional Application No. 63/272,971, filed Oct. 28, 2021, which is herein incorporated by reference in its entirety.

BACKGROUND

Electrocardiograms (ECGs) use electrodes positioned on a patient's body to detect the patient's heartbeat. The measurements from an ECG are typically displayed as a wave signal, with the heartbeat represented by crests and troughs in the wave. Different cardiac events and conditions can be detected by monitoring various characteristics of the wave signal (e.g., characteristics of the p-wave, QRS complex, and t-wave of an individual heartbeat).

Machine learning models have been applied to ECG wave signals to detect cardiac events. A challenge faced by these machine learning systems is the accurate identification of the component wave signals generated by a heartbeat (e.g., a p-wave, QRS complex, and t-wave). These inaccurate identifications lead to certain cardiac conditions being misdiagnosed or not diagnosed, jeopardizing the patient's health. Making matters worse, certain cardiac conditions (e.g., ectopy) cause portions of successive heartbeats to overlap in the ECG measurement. For example, the t-wave of a heartbeat may overlap with the p-wave of the next heartbeat, which makes it even more difficult for the machine learning systems to accurately identify the t-wave and the p-wave.

OVERVIEW

According to one example ("Example 1"), a method includes dividing electrocardiogram measurements of a patient into a plurality of segments that include a first portion of the electrocardiogram measurements corresponding to a first heartbeat of the patient and a second portion of the electrocardiogram measurements corresponding to the first heartbeat and a second heartbeat of the patient. The method may also include analyzing the second portion of the electrocardiogram measurements to identify a set of features of the second portion of the electrocardiogram measurements and adjusting the set of features based at least on the first portion of the electrocardiogram measurements and the second portion of the electrocardiogram measurements. The method may further include predicting, based on the adjusted set of features, a region in the second portion of the electrocardiogram measurements comprising a p-wave generated by the second heartbeat.

According to another example ("Example 2"), further to the method of Example 1, the method may also include predicting, based on the adjusted set of features, regions in the second portion of the electrocardiogram measurements comprising a t-wave generated by the second heartbeat and a QRS complex generated by the second heartbeat.

According to another example ("Example 3"), further to the method of any one of Examples 1-2, the region in the second portion of the electrocardiogram measurements comprises both the p-wave and a t-wave generated by the first heartbeat.

According to another example ("Example 4"), further to the method of any one of Examples 1-3, the first portion of the electrocardiogram measurements and the second portion of the electrocardiogram measurements are of a same duration.

According to another example ("Example 5"), further to the method of any one of Examples 1-4, analyzing the second portion of the electrocardiogram measurements to identify the set of features is performed using a deep neural network.

According to another example ("Example 6"), further to the method of any one of Examples 1-5, adjusting the set of features is performed using a long short-term memory circuit.

According to another example ("Example 7"), further to the method of any one of Examples 1-6, the method may also include predicting, based at least on the p-wave, a cardiac event in the patient.

According to another example ("Example 8"), further to the method of any one of Examples 1-7, predicting the region comprising the p-wave comprises predicting a start time of the p-wave and an end time of the p-wave.

According to another example ("Example 9"), further to the method of any one of Examples 1-8, the second heartbeat occurs after the first heartbeat.

According to one example ("Example 10"), an apparatus includes a memory; and a hardware processor communicatively coupled to the memory, the hardware processor configured to: divide electrocardiogram measurements of a patient into a plurality of segments comprising a first portion of the electrocardiogram measurements corresponding to a first heartbeat of the patient and a second portion of the electrocardiogram measurements corresponding to the first heartbeat and a second heartbeat of the patient, analyze the second portion of the electrocardiogram measurements to identify a set of features of the second portion of the electrocardiogram measurements, adjust the set of features based at least on the first portion of the electrocardiogram measurements and the second portion of the electrocardiogram measurements, and predict, based on the adjusted set of features, a region in the second portion of the electrocardiogram measurements comprising a p-wave generated by the second heartbeat.

According to another Example ("Example 11"), further to the apparatus of Example 10, the hardware processor further configured to predict, based on the adjusted set of features, regions in the second portion of the electrocardiogram measurements comprising a t-wave generated by the second heartbeat and a QRS complex generated by the second heartbeat.

According to another Example ("Example 12"), further to the apparatus of Examples 10-11, the region in the second portion of the electrocardiogram measurements comprises both the p-wave and a t-wave generated by the first heartbeat.

According to another Example ("Example 13"), further to the apparatus of Examples 10-12, the first portion of the electrocardiogram measurements and the second portion of the electrocardiogram measurements are of a same duration.

According to another Example ("Example 14"), further to the apparatus of Examples 10-13, analyzing the second portion of the electrocardiogram measurements to identify the set of features is performed using a deep neural network.

According to another Example ("Example 15"), further to the apparatus of Examples 10-14, adjusting the set of features is performed using a long short-term memory circuit.

According to another Example ("Example 16"), further to the apparatus of Examples 10-15, the hardware processor further configured to predict, based at least on the p-wave, a cardiac event in the patient.

According to another Example ("Example 17"), further to the apparatus of Examples 10-16, predicting the region comprising the p-wave comprises predicting a start time of the p-wave and an end time of the p-wave.

According to another Example ("Example 18"), further to the apparatus of Examples 10-17, the second heartbeat occurs after the first heartbeat.

According to one example ("Example 19"), a method includes analyzing a first segment of electrocardiogram measurements corresponding to a first heartbeat and a second heartbeat of a patient to identify a set of features of the first segment of electrocardiogram measurements; adjusting the set of features based at least on the first segment and a second segment of electrocardiogram measurements corresponding to the first heartbeat; and predicting, based on the adjusted set of features, a region in the second segment of electrocardiogram measurements comprising a p-wave generated by the second heartbeat.

According to another example ("Example 20"), further to the method of Example 19, the method further includes predicting, based on the adjusted set of features, regions in the second segment of electrocardiogram measurements comprising a t-wave generated by the second heartbeat and a QRS complex generated by the second heartbeat.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Various aspects of the present disclosure are directed toward computing systems and methods that use machine learning to accurately identify the component wave signals generated by a heartbeat. The computing system uses a deep neural network to identify features in the segments of an electrocardiogram (ECG) wave signal. These features may be approximations of the p-wave, QRS complex, and t-wave in each segment. The computing system then applies a long short-term memory circuit to analyze the features in a segment using information from other segments and to adjust the features to hone the approximations of the p-wave, QRS complex, and t-wave. For example, these adjustments may account for portions of successive heartbeats that overlap in the ECG measurement. The computing system then uses the adjusted features to predict the start and end times of the p-wave, QRS complex, and t-wave. The computing system may also predict the peak time of the QRS complex. As a result, the computing system provides more accurate predictions of the timing of the component wave signals generated by a heartbeat, which provides more accurate diagnoses of cardiac events and conditions, in certain embodiments.

Figure 1:
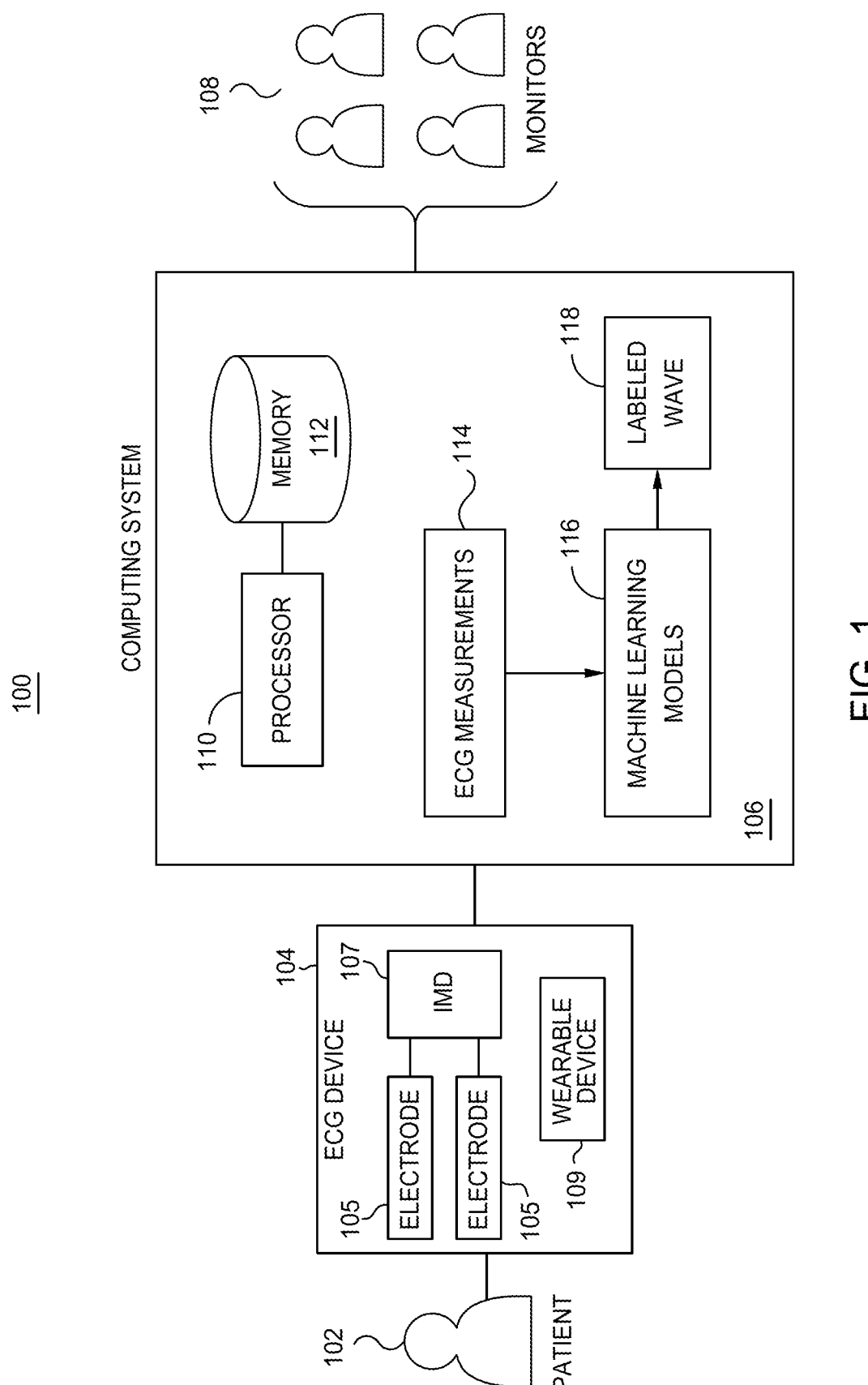
FIG. 1 illustrates an example system, in accordance with various aspects of the present disclosure.

FIG. 1 illustrates an example system 100. As seen in FIG. 1, the system 100 includes an ECG device 104 and a computing system 106. The computing system 106 may apply or execute one or more machine learning models to ECG measurements provided by the ECG device 104 to identify component wave signals generated by a heartbeat of a patient 102. In certain instances, the computing system 106 may increase accurate detection of the component wave signals, which can lead to more accurate diagnoses of cardiac events or conditions in the patient 102. For example, previous systems that used a manual process or a machine learning process had difficulty identifying the p-waves, QRS complexes, and t-waves of heartbeats when cardiac conditions (e.g., ectopy) caused the ECG measurements for successive heartbeats to overlap. For example, when the t-wave of a first heartbeat overlapped the p-wave of a second heartbeat, the previous systems could not accurately discern when the t-wave ended or when the p-wave began, which resulted in an inaccurate determination of the length or duration of the t-wave and p-wave. The inaccurate length or duration of the t-wave and p-wave would lead to inaccurate diagnoses of cardiac conditions. The system 100 may use a deep neural network and a long short-term memory circuit to identify and locate the component wave signals in ECG measurements, even when the ECG measurements for successive heartbeats overlap. The system 100 may first use the deep neural network to approximate the p-waves, QRS complexes, and t-waves and then the long short-term memory circuit to hone these approximations using the ECG measurements from other heartbeats as references, which may reveal where component wave signals in overlapping ECG measurements begin and end (e.g., where overlapping t-waves and p-waves begin and end). As a result, the system 100 may provide a more accurate determination of the length or duration of the component wave signals, which results in more accurate diagnoses of cardiac conditions.

The ECG device 104 may be connected, placed, attached to or implanted in the patient 102 to detect a heartbeat in the patient 102. The ECG device 104 may include one or more electrodes 105 that adhere or attach to the body of the patient 102. In other instances, the ECG device 104 may include one or more electrodes 105 arranged with, for example, an implantable medical device (IMD) 107 subcutaneously implanted in a chest, abdomen, or other parts of the patient 102. Examples of the IMD 107 may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The ECG device 104 alternatively or additionally may include a subcutaneous medical device such as a subcutaneous monitor or diagnostic device, external monitoring or therapeutic medical devices such as automatic external defibrillators (AEDs) or Holter monitors, or wearable medical devices 109 such as patch-based devices, smart watches, or smart accessories.

The ECG device 104 may include one or more wearable devices 109 (e.g., smartwatch), a portable computing device (e.g., smartphone), a medical device (e.g., a wearable medical device (WMD)), and/or the like. For example, the ECG device 104 may include a control device, a monitoring device, a respiratory device, a pacemaker, a cardiac resynchronization therapy (CRT) device and/or the like, and may be a wearable device and/or medical device known in the art or later developed, for sensing physiological parameters of the patient 102, providing therapy and/or diagnostic data about the patient 102 and/or the ECG device 104. In various embodiments, the ECG device 104 may include inhaler functionality, nebulizer functionality, ventilating functionality, defibrillation, and pacing/CRT capabilities (e.g., a CRT-D device). In embodiments, the ECG device 104 may be wearable on the patient 102 and may be configured to monitor (e.g., sense and/or record) physiological parameters associated with patient 102 (e.g., respiratory system, and/or circulatory system). In embodiments, the ECG device 104 may be configured to record physiological parameters such as, for example, one or more respiratory signals, cardiac electrical signals, spirometry, oximetry, arterial blood gas measurements, heart sounds, heart rate, blood pressure measurements, oxygen saturations, and/or the like.

The ECG device 104 may include any type of medical device (e.g., a wearable medical device (WMD) 109, an implantable medical device (IMD) 107, etc.) that senses one or more physiological signals of the patient 102, administers one or more therapies, and/or the like, and may include any number of different components of a medical device. For example, the ECG device 104 may include a control device, a monitoring device, a respiratory device, a pacemaker, an implantable cardioverter defibrillator (ICD), a cardiac resynchronization therapy (CRT) device, a neurostimulation device, a drug delivery device, a muscular stimulation device, an optimal or audio stimulation device, and/or the like, and may be a medical device known in the art or later developed, for sensing physiological signals, providing therapy and/or diagnostic data about the patient and/or the ECG device 104. In various embodiments, the ECG device 104 may include a drug delivery functionality (e.g., an inhaler functionality, a nebulizer functionality and/or the like), ventilating functionality, defibrillation, an air filtration functionality, a smoking cessation functionality, an oxygen delivery functionality, a volatile compound release functionality, and/or pacing/CRT capabilities (e.g., a CRT-D device). In embodiments, the ECG device 104 may be implanted subcutaneously within an implantation location or pocket in the patient's 102 chest or abdomen and may be configured to monitor (e.g., sense and/or record) physiological parameters associated with one or more body systems of the patient 102 (e.g., the respiratory system, the nervous system, and/or the circulatory system). In embodiments, the ECG device 104 may be an implantable respiratory monitor, an implantable cardiac monitor (ICM) (e.g., an implantable diagnostic monitor (IDM), an implantable loop recorder (ILR), etc.) configured to record physiological parameters such as, for example, one or more respiratory signals, cardiac electrical signals, spirometry, oximetry, arterial blood gas measurements, heart sounds, heart rate, blood pressure measurements, oxygen saturations, and/or the like.

By way of example, the ECG device 104 may be coupled to a lead system that may include one or more transvenously, subcutaneously, or non-invasively placed leads or catheters. Each lead or catheter may include the one or more electrodes.

When the patient's 102 heart beats, the electrodes detect the heartbeat and the ECG device 104 converts the heartbeat to an electric signal. For example, the electric signal may be a voltage signal whose magnitude increases or decreases depending on the detected heartbeat. The ECG device 104 communicates the electric signal representing the heartbeat of the patient 102 to the computing system 106 for analysis. The ECG device 104 may communicate device data to the computing system 106 via a communication link. The communication link may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible. If the patient 102 has a cardiac condition or experiences a cardiac event, the electric signal from the ECG device 104 may include an abnormality that indicates the cardiac condition or event.

The computing system 106 receives the electric signal representing the heartbeat from the ECG device 104. The computing system 106 applies one or more machine learning models to the electric signal to identify component wave signals generated by the heartbeat. In particular embodiments, the computing system 106 provides a more accurate prediction of the component wave signals generated by the heartbeat, which leads to more accurate diagnoses of cardiac events or conditions. As seen in FIG. 1, the computing system 106 includes a processor 110 and a memory 112 that perform the actions or functions of the computing system 106 described herein.

The processor 110 may include electronic circuitry, including, but not limited to one or a combination of microprocessors, microcontrollers, application specific integrated circuits (ASIC), application specific instruction set processor (ASIP), and/or state machines, that communicatively couples to memory 112 and controls the operation of the computing system 106. The processor 110 may be 8-bit, 16-bit, 32-bit, 64-bit or of any other suitable architecture. The processor 110 may include an arithmetic logic unit (ALU) for performing arithmetic and logic operations, processor registers that supply operands to the ALU and store the results of ALU operations, and a control unit that fetches instructions from memory and executes them by directing the coordinated operations of the ALU, registers and other components. The processor 110 may include other hardware that operates software to control and process information. The processor 110 executes software stored on the memory 112 to perform any of the functions described herein. The processor 110 controls the operation and administration of the computing system 106 by processing information (e.g., information received from the ECG device 104 and memory 112). The processor 110 is not limited to a single processing device and may encompass multiple processing devices. Insert standard text for the memory 112.

The memory 112 may store, either permanently or temporarily, data, operational software, or other information for the processor 110. The memory 112 may include any one or a combination of volatile or non-volatile local or remote devices suitable for storing information. For example, the memory 112 may include random access memory (RAM), read only memory (ROM), magnetic storage devices, optical storage devices, or any other suitable information storage device or a combination of these devices. The software represents any suitable set of instructions, logic, or code embodied in a computer-readable storage medium. For example, the software may be embodied in the memory 112, a disk, a CD, or a flash drive. In particular embodiments, the software may include an application executable by the processor 110 to perform one or more of the functions described herein.

The computing system 106 receives ECG measurements 114 from the ECG device 104. The ECG measurements 114 include an electric signal (e.g., a voltage signal) representing the heartbeat of the patient 102. The computing system 106 analyzes the ECG measurements 114 to determine component wave signals generated by the heartbeat of the patient 102.

The computing system 106 may analyze the ECG measurements 114 by applying one or more machine learning models 116 to the ECG measurements 114. For example, the computing system 106 may apply a deep neural network to the ECG measurements 114 to identify features within the ECG measurements 114. These features may be approximations of the p-waves, QRS complexes, and t-waves generated by the heartbeat of the patient 102. The computing system 106 may also apply a long short-term memory circuit to the ECG measurements 114 to adjust the features identified by the deep neural network. Adjusting these features may hone the approximations of the component wave signals generated by the heartbeat of the patient 102. The computing system 106 may further apply a neural network (e.g., a dense layer of a neural network) to the adjusted features to determine the start times and end times of the component wave signals generated by the heartbeat of the patient 102. For example, the computing system 106 may determine the start times and end times of the p-waves, QRS complexes, and t-waves generated by the heartbeat of the patient 102. The computing system 106 produces a labeled wave 118, which identifies the start and end times of the component wave signals generated by the heartbeat of the patient 102.

The computing system 106 may communicate the labeled wave 118 to one or more monitors 108. The monitors 108 may include human operators and other computing systems that analyze the labeled wave 118 to detect cardiac events or conditions in the patient 102. The monitors 108 can use the identified start and end times of the component wave signals generated by the heartbeat of the patient 102 to determine whether the patient 102 is experiencing a cardiac event or has a cardiac condition.

In some embodiments, the computing system 106 analyzes the labeled wave 118 to determine whether the patient 102 is experiencing a cardiac event or has a cardiac condition. The computing system 106 communicates the determined cardiac event or condition to the monitors 108. The monitors 108 may prescribe an appropriate treatment for the identified cardiac condition or event, which improves the health of the patient 102.

Figure 2:
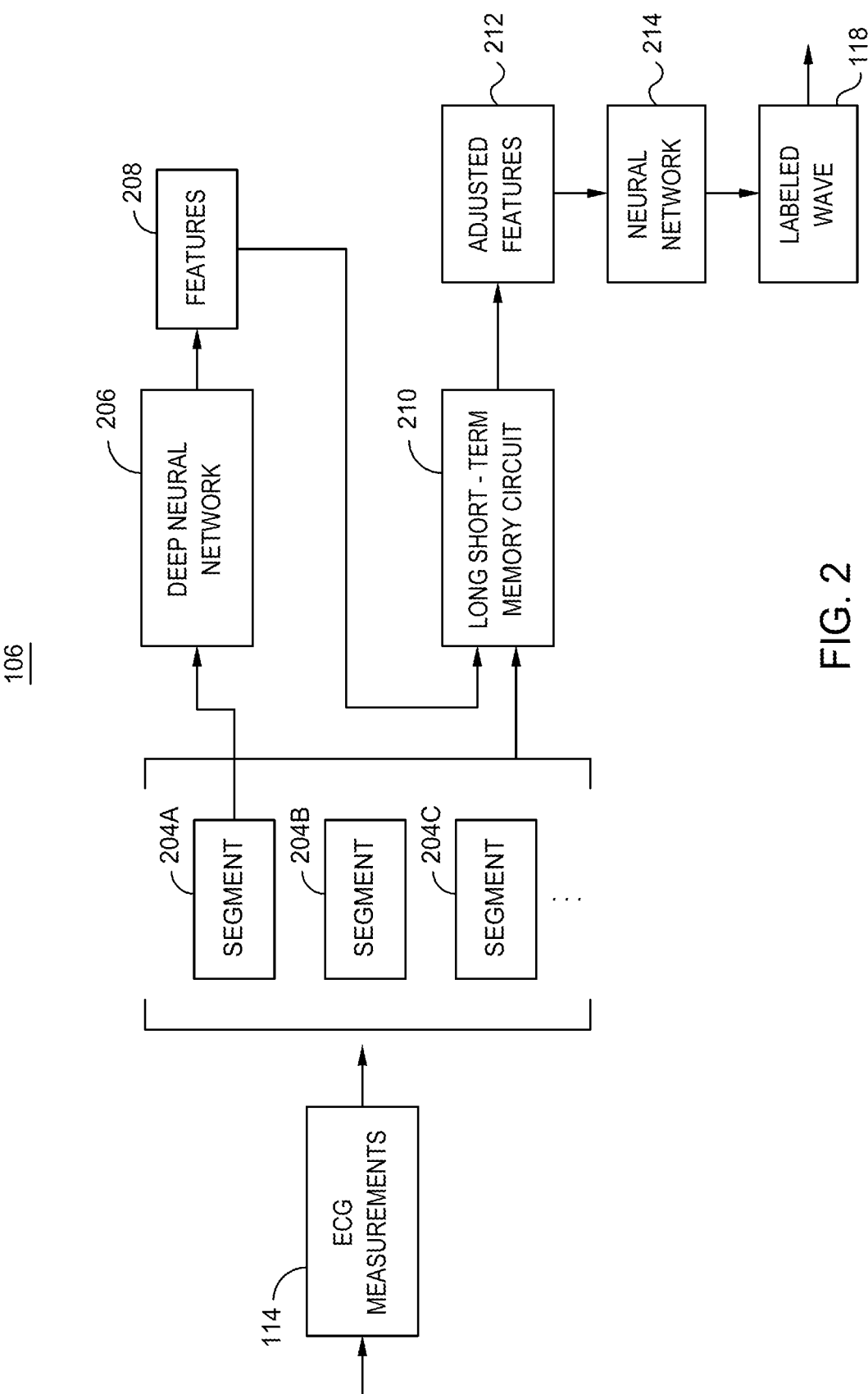
FIG. 2 illustrates an example computing system in the system of FIG. 1, in accordance with various aspects of the present disclosure.

FIG. 2 illustrates an example computing system 106 in the system 100 of FIG. 1. As seen in FIG. 2, the computing system 106 may apply one or more machine learning models to the ECG measurements 114 to produce the labeled wave 118. In certain instances, by using the machine learning models to produce the labeled wave 118, the labeled wave 118 includes a more accurate identification of the component wave signals generated by the heartbeat of a patient 102, which leads to more accurate diagnoses of cardiac events or conditions.

The computing system 106 receives ECG measurements 114 from the ECG device 104 shown in FIG. 1. The ECG measurements 114 include an electrical signal representing the heartbeats of a patient 102. The electrical signal includes component wave signals generated by the heartbeats. For example, the electrical signal includes the p-waves, QRS complexes, and t-waves generated by the heartbeats. The computing system 106 analyzes the electrical signal in the ECG measurements 114 to identify the start and end times of the component wave signals generated by the heartbeats of the patient 102.

The computing system 106 may be configured to divide the ECG measurements 114 into segments 204. Each segment 204 may be a time slice of the electrical signal and encompasses one heartbeat of the patient 102. For example, each segment 204 may be a two-second slice of the electrical signal in the ECG measurements 114. Each slice may be centered on the beat peak of the heartbeat in that slice. The electrical signal in the ECG measurements 114 may represent any suitable number of heartbeats, and the computing system 106 may divide the electrical signal into any suitable number of segments 204. In one example, such as shown in FIG. 2, the computing system 106 may divide the ECG measurements 114 into a segment 204A, a segment 204B, and a segment 204C. Each of the segments 204A, 204B, and 204C may be a time slice of the electrical signal in the ECG measurements 114 that encompasses one heartbeat of the patient 102. The segments 204A, 204B, and 204C may encompass portions of the electrical signal in the ECG measurements 114 that represent successive heartbeats of the patient 102.

The computing system 106 may analyze the segments 204 individually using a deep neural network 206 to identify features 208 in each segment 204. The deep neural network 206 may be a machine learning model with multiple layers between input and output layers. For example, the deep neural network 206 may contain convolutional layers or fully connected layers. The deep neural network 206 may include batch normalization, dropout, pooling, non-linear activation functions, and residual connections. The deep neural network 206 analyzes each segment 204 and calculates the probability that features exist at various time points of each segment 204. The time points with the highest probabilities of being features are identified as the features 208. For example, the deep neural network 206 may analyze the electrical signal in the segment 204A to determine how the electrical signal changes within the segment 204A. The deep neural network 206 may identify changes with larger magnitudes as the features 208 within the segment 204. Because the electrical signal in the segment 204A represents one heartbeat of the patient 102, the identified features 208 may be approximations of the p-wave, QRS complex, and t-wave generated by that heartbeat.

Certain cardiac events or conditions (e.g., ectopy) may cause some component wave signals generated by successive heartbeats to overlap in the ECG measurements 114. An ectopic heart condition may cause the t-wave of a heartbeat to overlap with the p-wave of a successive heartbeat in the ECG measurements 114. As a result, the deep neural network 206 may experience difficulty accurately identifying the features 208 in the segments 204 of the ECG measurements 114. For example, the deep neural network 206 may experience difficulty identifying the p-wave in a heartbeat if that portion of the electrical signal also includes the t-wave from the previous heartbeat. The computing system 106 applies additional machine learning models to the features 208 identified by the deep neural network 206 to hone the identified features 208 to more accurately represent the component wave signals generated by the heartbeats of the patient 102.

The computing system 106 applies a long short-term memory circuit 210 to the features 208 identified by the deep neural network 206. The long short-term memory circuit 210 may execute a bi-directional recurrent neural network that uses information from other segments 204 to adjust the identified features 208 in a particular segment 204. Alternatively, the long short-term memory circuit 210 may execute any suitable type of recurrent neural network, such as a uni-directional recurrent neural network or a gated recurrent network. The long short-term memory circuit 210 may use information from the segments 204B and 204C to adjust the features 208 identified in the segment 204A. A cardiac event or condition may cause discrepancies in the electric signal in the segment 204A, but the cardiac event or condition may not cause the same discrepancy in all segments 204. The long short-term memory circuit 210 uses information from the other segments 204 to determine whether the features 208 identified in the segment 204A should be adjusted to more accurately identify the component wave signals generated by the heartbeat represented by the electric signal in the segment 204A. For example, if the long short-term memory circuit 210 determines that the feature 208 corresponding to the p-wave in the segment 204A is inaccurate as a result of a t-wave from a previous heartbeat overlapping with the p-wave in the segment 204A, the long short-term memory circuit 210 may adjust that feature 208 to more accurately capture the p-wave in the segment 204A. The long short-term memory circuit 210 may adjust the duration of the feature 208 such that the feature 208 more accurately aligns with the p-wave in the segment 204A. The long short-term memory circuit 210 may determine that the feature 208 does not accurately align with the p-wave in the segment 204A using information about p-waves generated by the heartbeat of the patient 102 in other segments 204, such as segment 204B and 204C. The long short-term memory circuit 210 may make these adjustments for other component wave signals, such as the QRS complexes and t-waves of the segments 204 to produce adjusted features 212 for each of the segments 204.

The computing system 106 can apply a neural network 214 to the adjusted features 212 to produce labeled waves 218. In some embodiments, the neural network 214 does not include an activation function, and, as a result, the neural network 214 performs a regression rather than a classification. The computing system 106 may apply a dense layer of the neural network 214 to the adjusted features 212. The dense layer may include neurons that receive input from every neuron in the previous layer of the neural network 214. The neural network 214 analyzes the adjusted features 212 to determine the start and end times of the p-waves, QRS complexes, and t-waves in the ECG measurements 114. For example, the neural network 214 may analyze the adjusted features 212 to identify certain features as corresponding to a p-wave, a QRS complex, or a t-wave. The neural network 214 then labels the starting time and end time of each of these component wave signals. In some embodiments, the neural network 214 also identifies a peak time of each QRS complex based on the adjusted features 212. After identifying the start and end times, the neural network 214 produces the labeled waves 118, which identify the start and end times of the p-waves, QRS complexes, and t-waves in the ECG measurements 114. The computing system 106 then communicates the labeled waves 118 to one or more monitors 108 for analysis.

Figure 3:
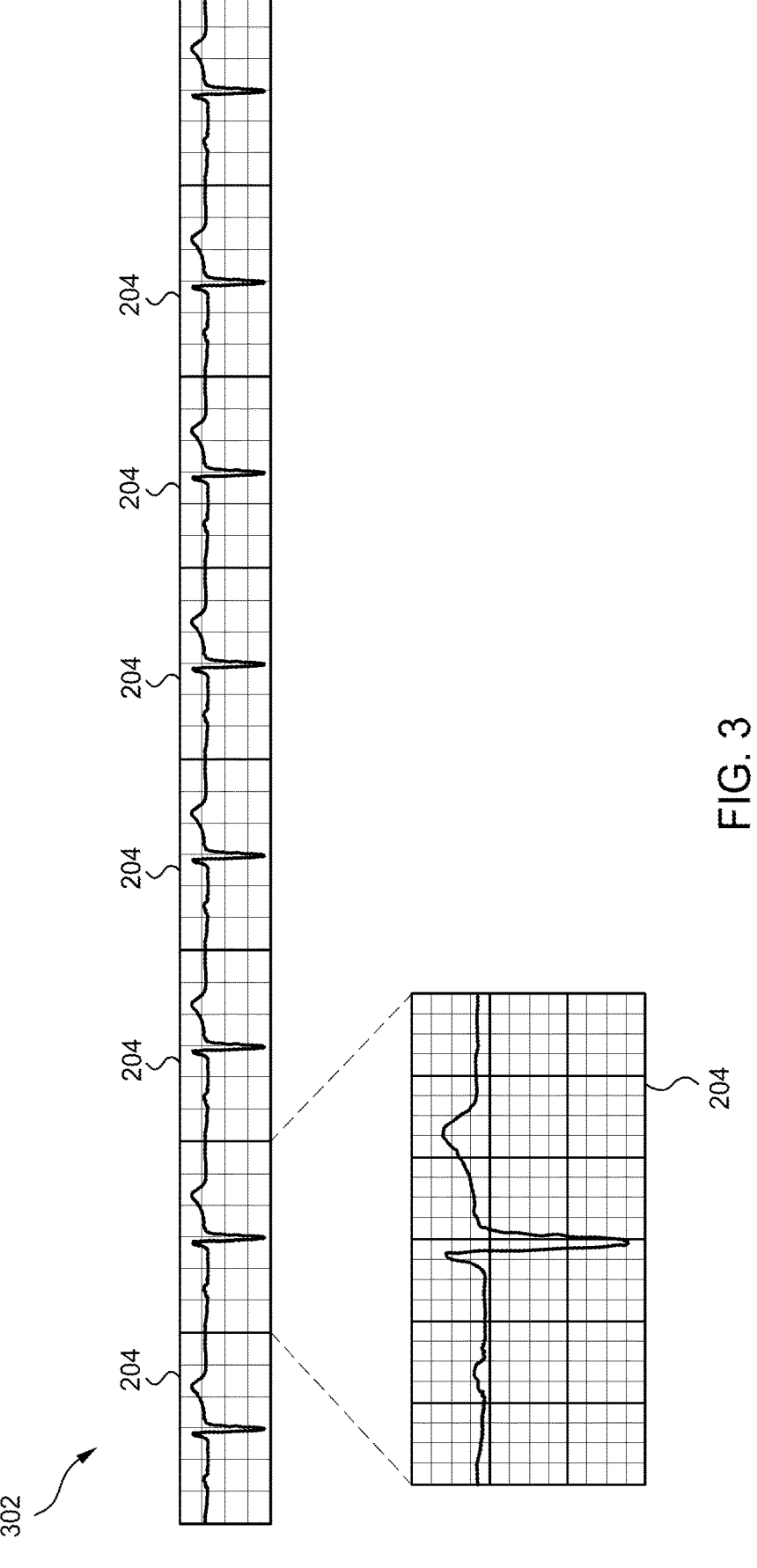
FIG. 3 illustrates an example ECG measurement in the system of FIG. 1, in accordance with various aspects of the present disclosure.

FIG. 3 illustrates an example ECG measurement 302 in the system 100 of FIG. 1. As seen in FIG. 3, the ECG measurement 302 includes an electrical signal representing the heartbeat of a patient 102. Because the heartbeat itself is generally periodic, the electric signal in the ECG measurement 302 also appears to be periodic. Furthermore, as seen in FIG. 3, the ECG measurement 302 is divided into segments 204. Each segment 204 is a time slice of the ECG measurement 302 and includes a portion of the electric signal. Generally, each of the segments 204 are the same duration. In some embodiments, each segment 204 is a two-second window of the electric signal in the ECG measurement 302. The electric signal in each segment 204 represents one heartbeat of the patient 102. Each segment 204 may also be centered on the beat peak of the electric signal for that segment 204.

Figure 4:
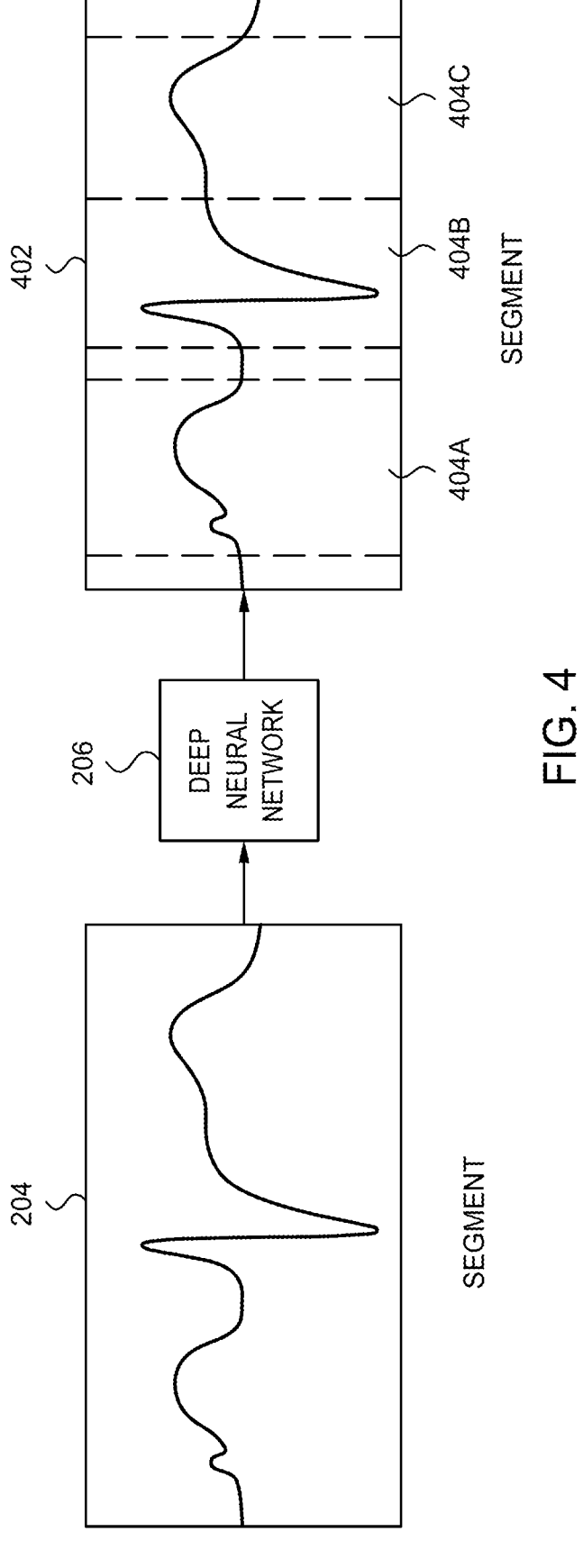
FIG. 4 illustrates an example operation of the computing system of FIG. 1, in accordance with various aspects of the present disclosure.

FIG. 4 illustrates an example operation of the computing system 106 of FIG. 1. As seen in FIG. 4, the deep neural network 206 analyzes a segment 204 to identify features in the electrical signal in the segment 204. As discussed previously, the deep neural network 206 may analyze the changes and transitions in the electrical signal in the segment 204 to identify features within the electrical signal. These features may be approximations of the component wave signals generated by a heartbeat.

As seen in FIG. 4, the deep neural network 206 may analyze the segment 204 to produce a segment 402 that includes the identified features 404A, 404B, and 404C. The feature 404A is an approximation of the p-wave generated by the heartbeat. The feature 404B is an approximation of the QRS complex generated by the heartbeat. The feature 404C is an approximation of the t-wave generated by the heartbeat. Although these approximations occupy different regions of the segment 204, the approximations may be inaccurate, especially if the segment 204 includes overlapping electrical signals generated by a previous heartbeat. For example, the feature 404A for the p-wave includes a portion of an overlapping t-wave generated by a previous heartbeat. As a result, the feature 404A has an inaccurate duration that is longer than it should be to include the p-wave and the t-wave. The computing system 106 applies additional analysis on the segment 402 to adjust and hone the identified features 404A, 404B, and 404C.

Figure 5:
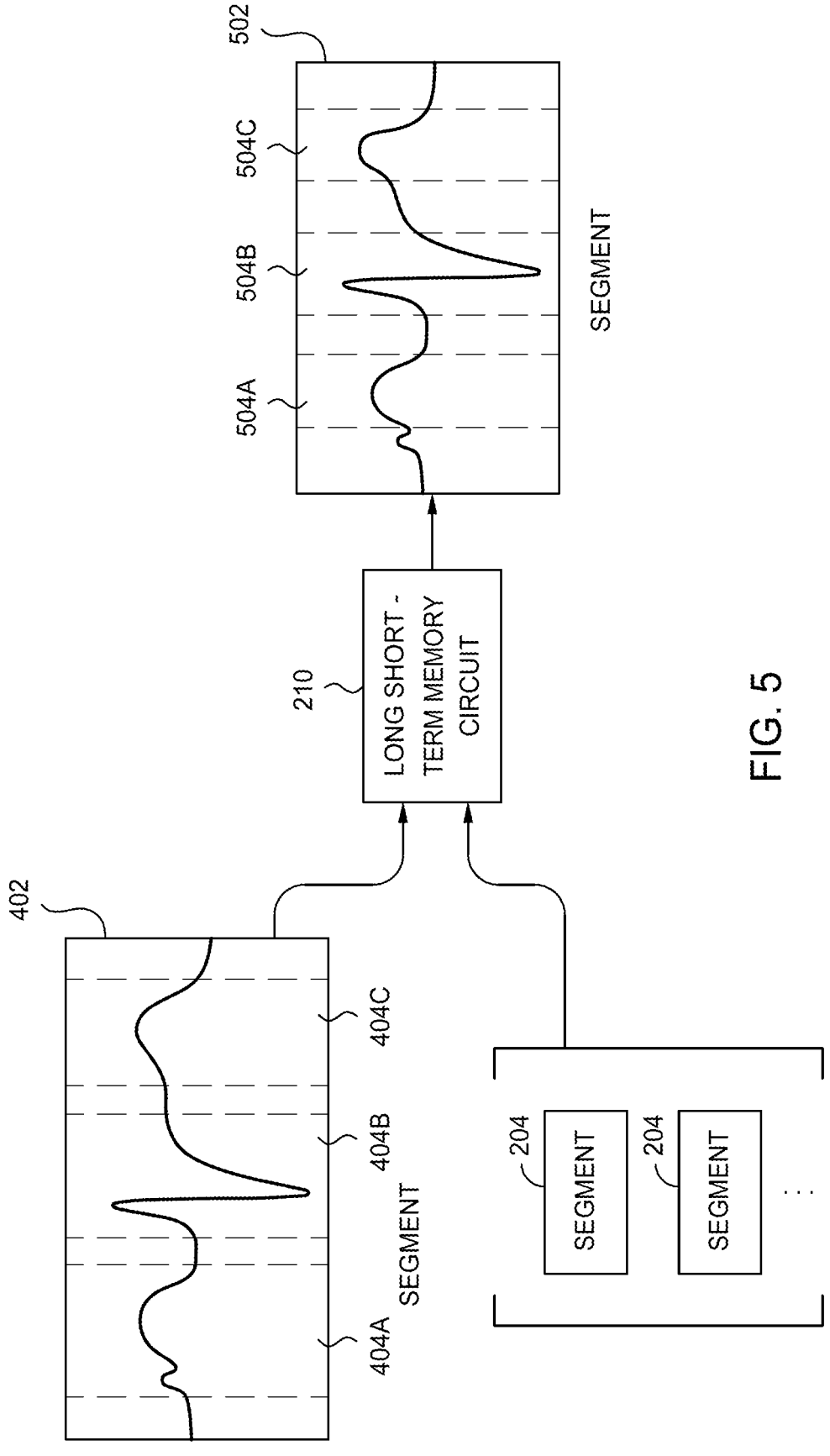
FIG. 5 illustrates an example operation of the computing system of FIG. 1, in accordance with various aspects of the present disclosure.

FIG. 5 illustrates an example operation of the computing system 106 of FIG. 1. As seen in FIG. 5, the computing system 106 uses the long short-term memory circuit 210 to adjust and hone the features 404A, 404B, and 404C identified in the segment 402. In certain embodiments, the adjustments produce more accurate approximations of the component wave signals generated by the heartbeat.

The long short-term memory circuit 210 receives the segment 402 with the identified features 404A, 404B, and 404C. The long short-term memory circuit 210 uses information from other segments 204 to analyze the segment 402 and its identified features 404A, 404B, and 404C. Specifically, the long short-term memory circuit 210 compares the segment 402 with other segments 204 to determine if there are discrepancies in the segment 402. The other segments 204 may be generated by heartbeats that occurred before or after the heartbeat that generated the segment 402. The long short-term memory circuit 210 then adjusts one or more of the features 404 to exclude these discrepancies and to produce the segment 502, which includes adjusted features 504. In the example of FIG. 5, the segment 502 includes the adjusted features 504A, 504B, and 504C, which occupy different regions of the segment 502. Because of the honing performed using the long short-term memory circuit 210, the adjusted features 504A, 504B, and 504C may more accurately encompass the p-wave, QRS complex, and t-wave when compared with the features 404A, 404B, and 404C.

As an example, the long short-term memory circuit 210 may determine, based on information from other segments 204, that the identified feature 404A is inaccurate in its duration. The long short-term memory circuit 210 may determine, using information about p-waves from the other segments 204, that the p-wave identified in the segment 402 is inaccurate as a result of that portion of the segment 402 also including an overlapping t-wave generated by a previous heartbeat. In response, the long short-term memory circuit 210 adjusts the boundaries of the feature 404A to exclude the t-wave generated by the previous heartbeat. As a result, the long short-term memory circuit 210 produces the feature 504A in the segment 502.

Figure 6:
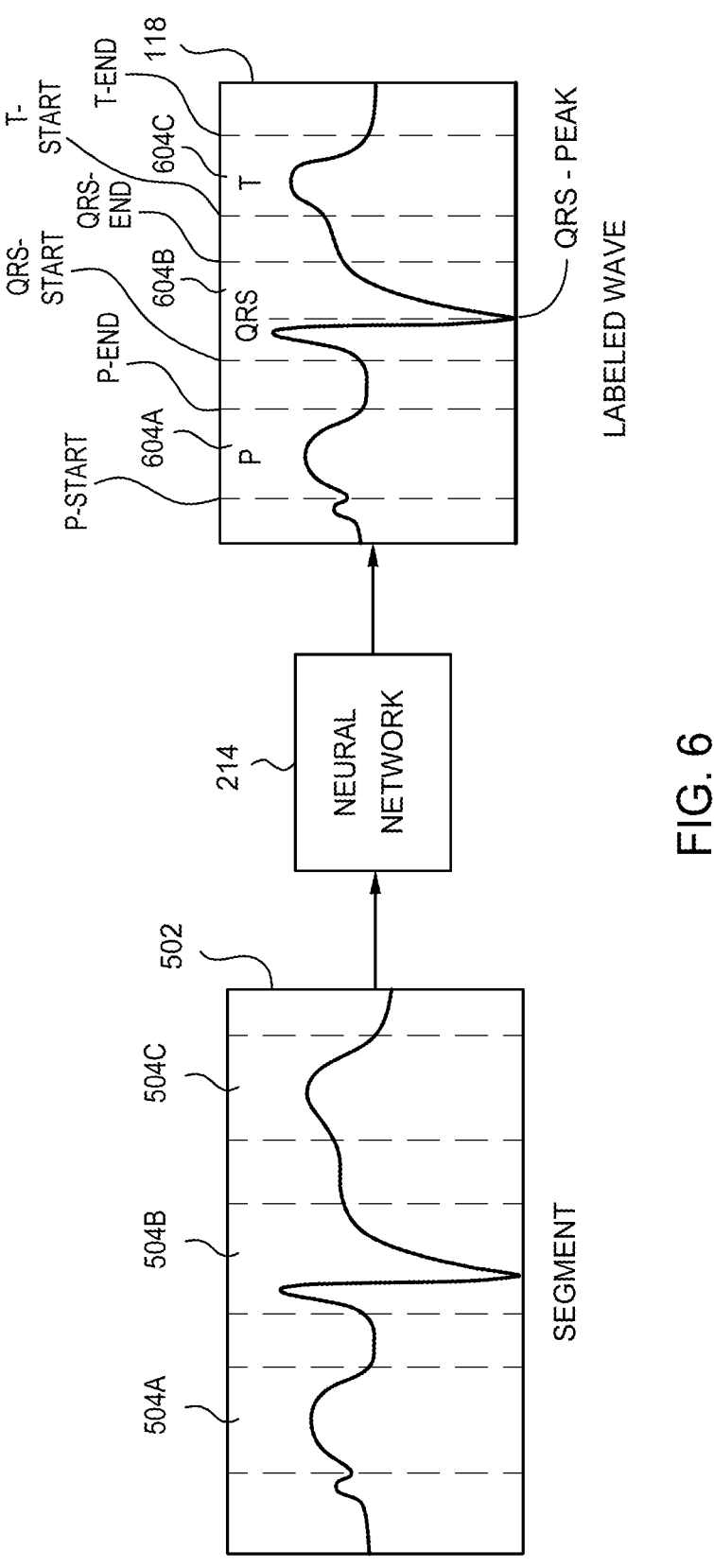
FIG. 6 illustrates an example operation of the computing system of FIG. 1, in accordance with various aspects of the present disclosure.

FIG. 6 illustrates an example operation of the computing system 106 of FIG. 1. As seen in FIG. 6, the computing system 106 applies a neural network 214 to the segment 502 produced by the long short-term memory circuit 210 shown in FIG. 5, to identify the start and end times of component wave signals. In this manner, the neural network 214 identifies the start and end times of p-waves, QRS complexes, and t-waves, which may be used to identify or diagnose cardiac events or conditions.

The neural network 214 analyzes the features 504A, 504B, and 504C in the segment 502 and determines which of these features 504A, 504B, and 504C corresponds to the p-wave, QRS complex, and t-wave. After identifying the p-wave, QRS complex, and t-wave, the neural network 214 identifies the start and end times of the p-wave, QRS complex, and t-wave based on the boundaries of the features 504A, 504B, and 504C. For example, these boundaries may represent the start and end times of the p-wave, QRS complex, and t-wave. As seen in FIG. 6, the neural network 214 produces the labeled wave 118, which identifies the p-wave 604A, the QRS complex 604B, and the t-wave 604C. Additionally, the labeled wave 118 identifies the start and end times of the p-wave 604A, the QRS complex 604B, and the t-wave 604C. In certain embodiments, the neural network 214 also identifies a peak time of the QRS complex. The labeled wave 118 identifies the peak time of the QRS complex (labeled as QRS-peak). As discussed below, the labeled wave 118 may then be used to detect or diagnose cardiac events or conditions in the patient 102.

Figure 7:
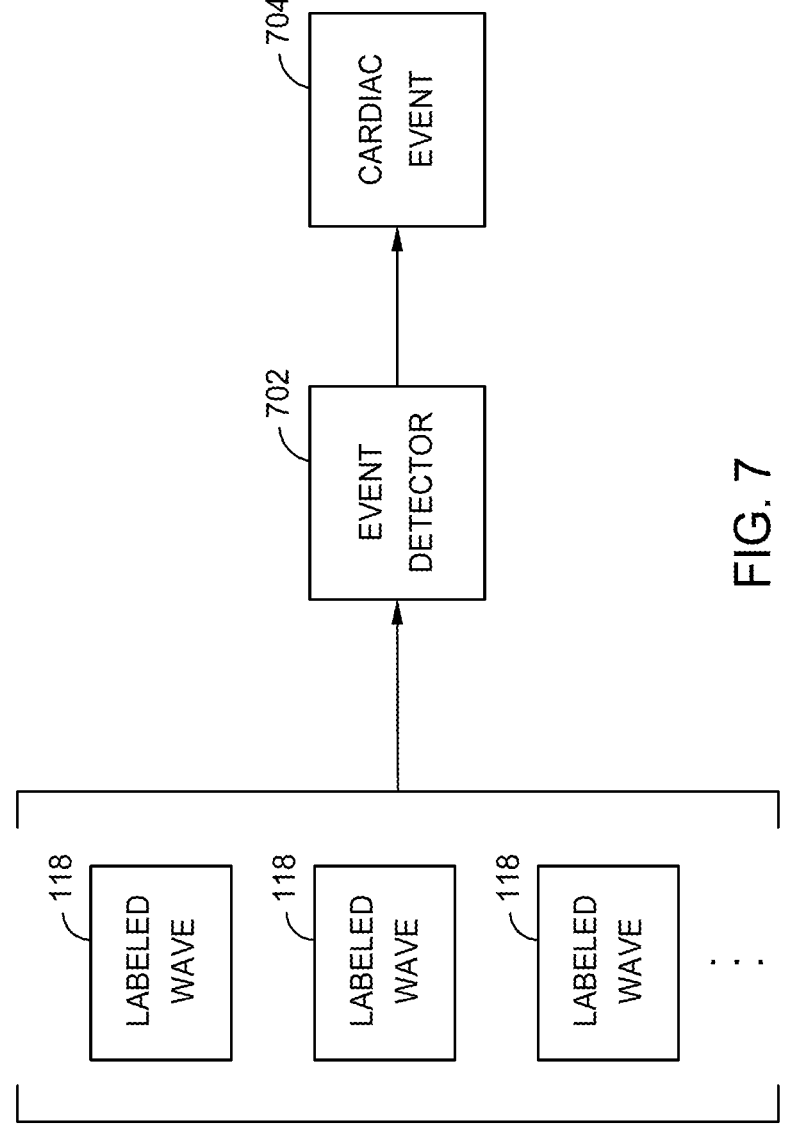
FIG. 7 illustrates an example operation of the computing system of FIG. 1, in accordance with various aspects of the present disclosure.

FIG. 7 illustrates an example operation of the computing system 106 of FIG. 1. The computing system 106 may use one or more labeled waves 118 to detect or identify cardiac events or conditions in a patient 102. Each of the labeled waves 118 may be for a segment 204 of the ECG measurement 114 shown in FIG. 2. Each labeled wave 118 identifies start and end times for the p-wave, QRS complex, and t-wave generated by the heartbeat for the corresponding segment 204.

The computing system 106 applies an event detector 702 to the labeled waves 118 to identify a cardiac event 704. The event detector 702 may be a machine learning model that can detect cardiac events 704 using the start and end times of the p-waves, QRS complexes, and t-waves in the labeled waves 118. For example, the event detector 702 can detect irregularities in the durations of the p-waves, QRS complexes, and t-waves or irregularities in the relative durations of the p-waves, QRS complexes, and t-waves. As another example, the event detector 702 may detect missing p-waves, QRS complexes, or t-waves in the labeled waves 118. Each of these detections may be indicative of a particular cardiac event 704. The event detector 702 outputs any detected cardiac events 704. In certain embodiments, the computing system 106 communicates a detected cardiac event 704 and/or the labeled waves 118 to a monitor 108 shown in FIG. 1. The monitor 108 then identifies the cardiac event 704 or determines a proper treatment for the cardiac event 704. As a result, the health of the patient 102 is improved. For example, the computing system 106 may detect, based on the labeled waves 118, that a patient 102 has ventricular ectopy, causing skipped heartbeats. The computing system 106 may communicate a message to the monitor 108 to alert the monitor 108 that the patient 102 is experiencing ventricular ectopy. Based on that alert, the monitor 108 may adjust the patient's 102 diet or exercise regimen. Additionally, the monitor 108 may perform one or more tests to determine the cause of the ectopy.

Figure 8:
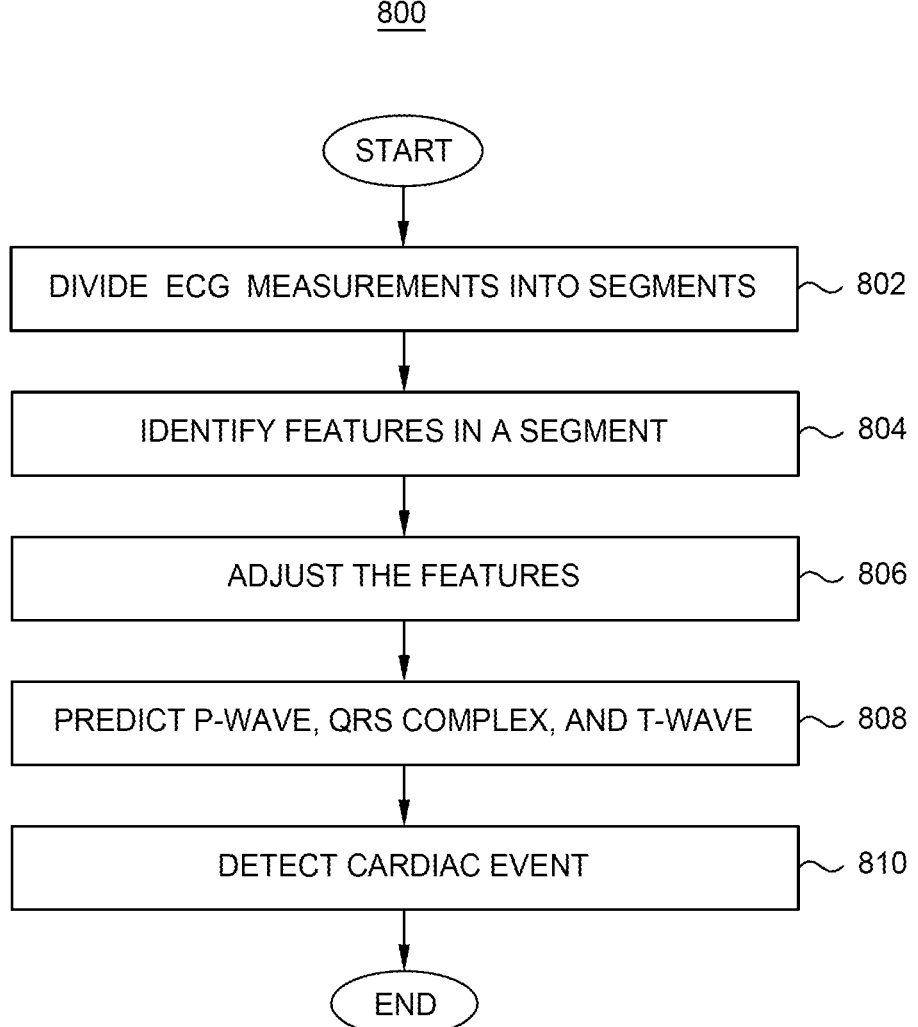
FIG. 8 is a flowchart of an example method performed in the system of FIG. 1, in accordance with various aspects of the present disclosure.

FIG. 8 is a flowchart of an example method 800 performed in the system 100 of FIG. 1. In particular embodiments, the computing system 106 performs the method 800. By performing the method 800, the computing system 106 accurately determines the start and end times of component wave signals generated by the heartbeat of a patient 102, which improves the accuracy of diagnoses of cardiac events and conditions in the patient 102.

The computing system 106 begins by dividing ECG measurements 114 into segments 204 in block 802. Each of the segments 204 is a time slice of the ECG measurements 114 and includes one heartbeat of the patient 102. Additionally, each time slice may be centered on the beat peak of that heartbeat. The computing system 106 applies one or more machine learning models to these segments 204 to identify the start and end times of component wave signals generated by the heartbeat.

In block 804, the computing system 106 identifies features 208 in a segment 204. The computing system 106 applies a deep neural network 206 to a segment 204 to identify the features 208. The deep neural network 206 may analyze the changes and transitions in the electric signal in the segment 204 to identify the features 208. The identified features 208 are approximations of component wave signals generated by the heartbeat for the segment 204. For example, the identified features 208 may be approximations of the p-wave, QRS complex, and t-wave generated by the heartbeat for the segment 204. Cardiac events or conditions may introduce discrepancies into the electric signal in the segment 204, and these discrepancies may cause the identified features 208 to include inaccuracies. For example, the identified features 208 may inaccurately approximate the p-wave generated by the heartbeat for the segment 204.

In block 806, the computing system 106 adjusts the identified features 208. The computing system 106 applies a long short-term memory circuit 210 to the identified features 208 to adjust the features 208. The long short-term memory circuit 210 uses information from other segments 204 to identify inaccuracies in the identified features 208. For example, the long short-term memory circuit 210 may determine, based on other segments 204, that the p-waves generated by the patient 102 have a certain shape or duration that is not shown in the identified features 208. In response, the long short-term memory circuit 210 adjusts the features 208 to more accurately capture the p-wave in a segment 204. For example, the computing system 106 may adjust the duration of the feature 208 corresponding to the p-wave.

In block 808, the computing system 106 predicts the start and end times of the p-waves, QRS complexes, and t-waves in the segments 204. The computing system 106 applies a neural network 214 to the adjusted features 212 produced by the long short-term memory circuit 210 to identify the p-waves, QRS complexes, and t-waves in the segments 204. In some embodiments, the computing system 106 applies a dense layer of the neural network 214 to the adjusted features 212 to identify the p-wave, QRS complex, and t-wave. The computing system 106 may apply the neural network 214 to identify the start and end times of the p-wave, QRS complex, and t-wave. Additionally, the computing system 106 may apply the neural network 214 to identify a peak time of the QRS complex. The computing system 106 produces a labeled wave 118 that identifies the p-wave, QRS complex, and t-wave within a segment 204. Additionally, the labeled wave 118 identifies the start and end times of the p-wave, QRS complex, and t-wave.

The computing system 106 detects a cardiac event 704 in block 810. The computing system 106 may apply an event detector 702 to the labeled waves 118 for the segments 204 to determine whether a cardiac event 704 is occurring in the patient 102. For example, the event detector 702 may determine that the patient 102 is experiencing a cardiac event 704 based on the durations of the p-waves, QRS complexes, and t-waves in the labeled waves 118. As another example, the event detector 702 may determine that the patient 102 is experiencing a cardiac event 704 based on certain p-waves, QRS complexes, or t-waves being missing from the labeled waves 118. The computing system 106 may communicate the detected cardiac event 704 to one or more monitors 108 for diagnosis and treatment.

In summary, a computing system 106 uses machine learning to accurately identify the component wave signals generated by a heartbeat. The computing system 106 uses a deep neural network 206 to identify features 208 in the segments 204 of an ECG wave signal. These features 208 may be approximations of the p-wave, QRS complex, and t-wave in each segment 204. The computing system applies a long short-term memory circuit 210 to analyze the features 208 in a segment 204 using information from other segments 204 and to adjust the features 208 to hone the approximations of the p-wave, QRS complex, and t-wave. The computing system 106 uses the adjusted features 212 to predict the start and end times of the p-wave, QRS complex, and t-wave. The computing system 106 may also predict the peak time of the QRS complex. As a result, the computing system 106 provides more accurate predictions of the timing of the component wave signals generated by a heartbeat, which provides more accurate diagnoses of cardiac events and conditions, in certain embodiments.

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The above detailed description is intended to be illustrative, and not restrictive. The scope of the disclosure should, therefore, be determined with references to the appended claims, along with the full scope of equivalents to which such claims are entitled.

I claim:

1. A method comprising:
dividing electrocardiogram (ECG) measurements of a patient into a plurality of segments comprising a first segment of the ECG measurements corresponding to a first heartbeat of the patient and a second segment of the ECG measurements corresponding to the first heartbeat and a second heartbeat of the patient;
analyzing the second segment of the ECG measurements to identify a set of features of the second segment of the ECG measurements, wherein the set of features comprise of portions of heartbeats;

adjusting a duration of at least one feature of the set of features based at least on the first segment of the ECG measurements and the second segment of the ECG measurements;
determining, based on the adjusted duration of the at least one feature of the set of features, a region in the second segment of the ECG measurements comprising a p-wave generated by the second heartbeat; and
determining, based on the determined region in the second segment, whether a cardiac abnormality is occurring in a patient.

2. The method of claim 1, further comprising determining, based on the adjusted duration of the at least one feature of the set of features, regions in the second segment of the ECG measurements comprising a t-wave generated by the second heartbeat and a QRS complex generated by the second heartbeat.

3. The method of claim 1, wherein the region in the second segment of the ECG measurements comprises both the p-wave and a t-wave generated by the first heartbeat.

4. The method of claim 1, wherein heartbeats of the first segment of the ECG measurements and heartbeats of the second segment of the ECG measurements are of a same duration.

5. The method of claim 1, wherein the analyzing the second segment of the ECG measurements to identify the set of features is performed using a deep neural network to identify changes with larger magnitudes as the set of features within the second segment than magnitudes of a corresponding set of features within the first segment.

6. The method of claim 1, wherein the adjusting the durations of the at least one feature of the set of features is performed using a long short-term memory circuit to adjust the duration of the at least one feature such that the at least one feature aligns with the p-wave in the second segment.

7. The method of claim 1, further comprising determining a treatment for determined cardiac abnormality occurring in the patient.

8. The method of claim 1, wherein determining the region comprising the p-wave comprises determining a start time of the p-wave and an end time of the p-wave.

9. The method of claim 1, wherein the second heartbeat occurs after the first heartbeat.

10. An apparatus comprising:
a memory; and
a hardware processor communicatively coupled to the memory and configured to:
divide electrocardiogram (ECG) measurements of a patient into a plurality of segments comprising a first segment of the ECG measurements corresponding to a first heartbeat of the patient and a second segment of the ECG measurements corresponding to the first heartbeat and a second heartbeat of the patient,
analyze the second segment of the ECG measurements to identify a set of features of the second segment of the ECG measurements, wherein the set of features comprise of portions of heartbeats,
adjust a duration of at least one feature of the set of features based at least on the first segment of the ECG measurements and the second segment of the ECG measurements,
determine, based on the adjusted duration of the at least one feature of the set of features, a region in the second segment of the ECG measurements comprising a p-wave generated by the second heartbeat; and determine, based on the determined region in the second segment, whether a cardiac abnormality is occurring in a patient.

11. The apparatus of claim 10, wherein the hardware processor is further configured to determine, based on the adjusted duration of the at least one feature of the set of features, regions in the second segment of the ECG measurements comprising a t-wave generated by the second heartbeat and a QRS complex generated by the second heartbeat.

12. The apparatus of claim 10, wherein the region in the second segment of the ECG measurements comprises both the p-wave and a t-wave generated by the first heartbeat.

13. The apparatus of claim 10, wherein heartbeats of the first segment of the ECG measurements and heartbeats of the second segment of the ECG measurements are of a same duration.

14. The apparatus of claim 10, wherein the analyze the second segment of the ECG measurements to identify the set of features is performed using a deep neural network to identify changes with larger magnitudes as the set of features within the second segment than magnitudes of a corresponding set of features within the first segment.

15. The apparatus of claim 10, wherein adjusting the duration of the at least one feature of the set of features is performed using a long short-term memory circuit to adjust the duration of the at least one feature such that the at least one feature aligns with the p-wave in the second segment.

16. The apparatus of claim 10, wherein the hardware processor is further configured to determine a treatment for determined cardiac abnormality occurring in the patient.

17. The apparatus of claim 10, wherein the determining the region comprising the p-wave comprises determining a start time of the p-wave and an end time of the p-wave.

18. The apparatus of claim 10, wherein the second heartbeat occurs after the first heartbeat.

19. A method comprising:

analyzing a first segment of electrocardiogram (ECG) measurements corresponding to a first heartbeat and a second heartbeat of a patient to identify a set of features of the first segment of ECG measurements, wherein the set of features comprise of portions of heartbeats;

adjusting a duration of at least one feature of the set of features based at least on the first segment and a second segment of ECG measurements corresponding to the first heartbeat;

determining, based on the adjusted duration of the at least one feature of the set of features, a region in the second segment of ECG measurements comprising a p-wave generated by the second heartbeat; and determining, based on the determined region in the second segment, whether a cardiac abnormality is occurring in a patient.

20. The method of claim 19, further comprising determining, based on the adjusted duration of the at least one feature of the set of features, regions in the second segment of ECG measurements comprising a t-wave generated by the second heartbeat and a QRS complex generated by the second heartbeat.

* * * * *